United States Patent [19]

Nichols

[11] Patent Number: 5,223,267
[45] Date of Patent: Jun. 29, 1993

[54] ANALGESIC COMPOSITIONS

[75] Inventor: Larry D. Nichols, Arlington, Mass.

[73] Assignee: Purepac, Inc., Elizabeth, N.J.

[21] Appl. No.: 869,107

[22] Filed: Apr. 14, 1992

Related U.S. Application Data

[63] Continuation of Ser. No. 619,485, Nov. 29, 1990, abandoned, which is a continuation-in-part of Ser. No. 358,690, May 30, 1989, Pat. No. 5,000,947.

[51] Int. Cl.$^5$ ............................................... A61K 9/14
[52] U.S. Cl. ..................................... 424/489; 424/69; 424/400; 424/401; 424/488; 424/499; 514/781; 514/887; 514/817; 514/951; 514/159; 514/165; 514/692
[58] Field of Search .................. 424/400, 488, 489

[56] References Cited

U.S. PATENT DOCUMENTS

| | | | |
|---|---|---|---|
| 3,824,085 | 7/1974 | Teng et al. | 44/7 B |
| 3,846,404 | 11/1974 | Nichols | 260/230 |
| 3,940,384 | 2/1976 | Teng | 260/226 |
| 3,985,298 | 10/1976 | Nichols | 239/54 |
| 4,016,254 | 4/1977 | Seager | 424/33 |
| 4,024,073 | 5/1977 | Shimizu et al. | 252/316 |
| 4,029,726 | 6/1977 | Nichols | 264/41 |
| 4,067,824 | 1/1978 | Teng et al. | 252/522 |
| 4,128,507 | 12/1978 | Mitzner | 252/522 |
| 4,193,989 | 3/1980 | Teng et al. | 424/60 |
| 4,369,173 | 1/1983 | Causland et al. | 424/35 |
| 4,383,988 | 5/1983 | Teng et al. | 424/68 |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,702,916 | 10/1987 | Geria | 424/400 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 427/27 |
| 4,755,433 | 7/1988 | Patel et al. | 428/422 |
| 4,888,420 | 12/1989 | Steiner et al. | 536/76 X |
| 4,925,667 | 5/1990 | Fellows et al. | 424/401 |
| 4,940,588 | 7/1990 | Sparks et al. | 424/490 |
| 4,952,402 | 8/1990 | Sparks et al. | 424/419 |
| 5,000,947 | 3/1991 | Nichols | 424/69 |
| 5,013,473 | 5/1991 | Norbury et al. | 252/174 |

OTHER PUBLICATIONS

Moleculon, Inc., Form 10-K for FY ended Nov. 30, 1988, pp. 1-7.

*Primary Examiner*—Thurman K. Page
*Assistant Examiner*—James M. Spear
*Attorney, Agent, or Firm*—Thomas J. Engellenner; James E. Maslow

[57] ABSTRACT

Liquefiable powder compositions are disclosed for the delivery of topical analgesics. In particular, microporous cellulosic powders, such as cellulose acetates or nitrates, are disclosed as high liquid content vehicles for the delivery of liquid analgesic preparations. The resulting powders permit the application of the analgesic preparation by simply rubbing or otherwise applying the formulation onto the skin in such a manner that the powder liquefies and appears to vanish. Upon application, the frangible liquid loaded cellulosic powders break up into minute particles that do not pass easily beyond the initial layers of the skin, but do permit the slow release of the analgesic agent for absorption into the skin.

14 Claims, No Drawings

5,223,267

ANALGESIC COMPOSITIONS

REFERENCE TO RELATED APPLICATION

This is a continuation of Ser. No. 619,485, filed Nov. 29, 1990, now abandoned which is a continuation in part of U.S. Ser. No. 358,690 filed May 30, 1989, now U.S. Pat. No. 5,000,947.

BACKGROUND OF THE INVENTION

The technical field of this invention is the topical application of personal care agents and, in particular, methods and compositions for topical application of local analgesics.

The topical use of mild counter-irritants to reduce the discomfort of fatigued muscles and irritated joints is a long-standing practice throughout the world. Some of the most commonly employed counter-irritants, alone or in combination, include menthol, eucalyptol, methyl salicylate and camphor. More recently, both nonsteroidal anti-inflammatory (NSAI) agents and steroidal anti-inflammatory (SAI) agents have come into similar topical use, especially among athletes and individuals suffering from arthritis. The most commonly used NSAIs are derivatives of salicylic acid, such as acetylsalicylic acid (aspirin) and triethanolamine salicylate (TEAS). One of the most effective of the standard counter-irritants, methyl salicylate, owes part of its efficacy to the fact that it is also an NSAI. The most commonly used SAIs include hydrocortisone creams.

Ideal compositions for use as topical analgesics should disperse easily onto the skin and deliver their active ingredients in a way that allows a portion to penetrate the skin rapidly, for prompt relief, while also maintaining an active reservoir on the surface of the skin to provide sustained relief. At the same time, the composition should be formulated to enable neat and easy application with a minimum of mess and discomfort, and with a low potential for staining clothes.

Most topical analgesic preparations are creams or lotions which do not fully satisfy these requirements for convenient, neat, comfortable application, prompt relief, and sustained delivery. There thus exists a need for better topical analgesic preparations offering improvements in convenience and efficacy.

SUMMARY OF THE INVENTION

Liquefiable powder compositions are disclosed for the delivery of topical analgesics. In particular, microporous cellulosic powders, such as cellulose acetates of nitrates, are disclosed as high liquid content vehicles for the delivery of local analgesics to the skin. The resulting powders permit the application of counter-irritant and anti-inflammatory preparations simply by rubbing or otherwise applying the formulation to the skin in a manner which causes the powder to liquefy and appear to vanish. This behavior occurs because, upon application, the liquid-loaded cellulosic powder particles break up into invisibly minute fragments. These particles cannot themselves pass beyond the superficial layers of the skin, but they promptly exude part of their liquid payload as a thin film high suitable for percutaneous penetration, while retaining a portion to be delivered on demand as the original liquid layer becomes depleted.

Details of the formation of cellulosic powders can be found in the above-referenced parent application, U.S. Ser. No. 358,690, filed May 30, 1989 U.S. Pat. No. 5,000,947 and a commonly-owned, copending application entitled "Process for Producing Liquid-Loaded Powders", by Larry D. Nichols and John F. Cline, filed contemporaneously herewith, both of which are incorporated herein by reference. A preferred polymer liquid-loadable powder includes microporous cellulose triacetate prepared by the method of the above application, entitled "Process for Producing Liquid-Loaded Powders".

In one technique, the liquefiable powders or dry porous powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 micrometers in average diameter, preferably from about 5 to about 100 micrometers in average diameter, and typically are roughly microspherical in shape. They are further characterized by being microporous with interconnecting pores ranging in size from about one to about 500 nanometers and capable of holding liquid payloads of active agents.

The cellulosic powder can be formed from cellulosic polymers chosen rom the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

Compositions made in accordance with the present invention permit the delivery of effective amounts of analgesic ingredients without many of the problems normally associated with liquids, oils, creams, lotions and gels. By assisting in the distribution of analgesic agents uniformly over the skin and providing an invisible superficial reservoir to replace active ingredients as they are absorbed into the body or lost to the environment, the compositions of the invention enhance the efficacy, heighten the convenience, and improve the economy of self-ministered local analgesics.

Topical analgesic preparations which can be used in the practice of the invention include counter-irritants such as menthol, camphor, eucalyptol, methyl salicylate and derivatives or mixtures thereof, NSAIs such as aspirin, TEAS, ibuprofen derivatives, mixtures and the like, and SAIs such as hydrocortisone and other steroidal analogs. Such analgesics can be dissolved or dispersed in a liquid carrier to form a liquid analgesic preparation. Other active ingredients will occur to those skilled in the art, and may include NSAI/SAI compounds developed in the future. The cellulosic matrix of the liquefiable powders is broadly compatible with a wide range of aqueous, alcoholic and oil liquids, and even when particular active ingredients such as camphor or methyl salicylate would in pure form cause undue softening of the cellulosic polymer, mixtures with other active ingredients and/or excipients readily produce a powder with acceptable properties. In a similar way, solid components can be included in liquid-delivering powders by dissolving them in a suitable solvent, which may itself be chosen to provide a desirable degree of emolliency and moisturization.

Frequently, counter-irritants themselves cause discomfort if applied to the skin at excessively high concentrations, which may call for the use of diluents and extenders. Most standard topical and cosmetic liquids are suitable for use in liquefiable cellulosic powders when liquid formulations containing typical organic counter-irritants are to be diluted or extended. The common liquids include but are not limited to mineral oils, silicone oils, fatty esters, fatty alcohols, and lower molecular weight alcohols, glycols and esters. Ionic or high polar NSAI ingredients, such as aspirin, may require the use of solvent liquids such as light alcohols in which such polar and ionic compounds can be readily dissolved.

In various embodiments of the invention, the analgesic agent can be incorporated into frangible cellulosic microbeads to be used directly in powdered form, or mixed with other powders such as talc or starch to provide a drier feel, or compacted into cakes, or blended with binders and shaped into bars or sticks. In all such embodiments, application of the powder material to the skin distributes it substantially as a fragmented and liquefied carrier, which can provide prompt and prolonged analgesic action.

In one embodiment, the analgesic-loaded frangible cellulosic powder of the invention, such as in microbead form, can be formulated into a cream or lotion by admixture with a suitable liquid base, but without the use of potentially irritating surfactants or other stabilizers. Yet such creams are as stable as conventional stabilized emulsions. Liquefiable analgesic cellulosic powders are thus suitable for the preparation of stable, minimally irritating, hypoallergenic creams. Suitable liquid bases for cream or lotion embodiments include water, mineral or silicone oils, volatile silicones, and moisturizing agents such as glycerine or propylene glycol.

Suitable liquid bases for cream or lotion type embodiments include water, oils and moisturizing agents, such as glycerin or aloe vera gels. Additional ingredients can include stearic acid, silicone liquids, triethanolamine, petrolatum, cetyl alcohol, carbomers, and the like.

Regardless of the embodiment, various additives can be mixed with the liquid-loaded particles (or liquid base) including, for example, talc, cornstarch, waxes, silicones, additional analgesics, cosmetics, fragrances, lubricants, emollients, moisturizers, medications and other personal care agents, colorants, pearlescent agents, and mixtures of such additives.

In the compacted cake embodiments, the liquid loaded powders can be compacted to packing densities ranging from about 55 percent to about 75 percent, more preferably from about 60 percent to about 70 percent of the void-free density of the combined materials to yield cakes that are dry and firm and yet readily permit transfer of the formulation to the skin by finger or brush.

Such compacted cakes can be obtained by applying a pressure ranging from about 50 to about 80 PSI to a cellulosic powder which has been appropriately loaded with a liquid payload of the active agent. In the absence of other additives, the resulting shaped articles have a compacted density ranging from about 0.55 to about 0.75 gm/cc.

Sticks or bars incorporating liquefiable powders with active agent payloads can be made by a variety of techniques. For example, sticks can be formulated by compounding a liquefiable powder with fatty alcohols, fatty acids, and/or salts of fatty acid anions with metallic or alkanolamine cations to produce a stick having a soap as the binding agent.

Alternatively, stick compositions can be formed by compounding a liquefiable powder with soft, water-soluble polymers, such as polyethylene glycols or polypropylene glycols, to produce a stick having a soluble wax as the binding agent. Sticks can also be made up by compounding a liquefiable powder with silicones or with blends of liquids and solids, such as salts and/or propylene glycols, to produce sticks having a thick or partially-solidified slurry as the binding agent. In yet another approach, sticks can be formed by compounding a liquefiable powder with a fusible wax, including fatty esters, silicone waxes, polyglycol waxes and aliphatic waxes, and then applying heat and pressure to produce sticks having a wax as the binding agent. The above binding agents can be introduced directly, or as payload in a second portion of liquefiable powder to be blended with that carrying the active ingredient, for example. Other methods of stick production will readily occur to those skilled in the art and are consistent with the teachings of the present invention.

The invention will next be described in connection with certain exemplary methods and compositions. However, it should be clear that various additions, subtractions and changes can be made by those skilled in the art without departing from the spirit or scope of the invention. For example, various additives can be mixed together with the sunscreen loaded powder particles of the invention, including, for example, talc, cornstarch, waxes, silicones, cosmetics, fragrances, lubricants, emollients, moisturizers, medications and other personal care agents, as well as colorants, pearlescent agents, and mixtures of such additives.

In some applications, it may also be preferable to include a quantity of a dry cellulosic powder (e.g., less than 50 percent of the total cellulosic components) to provide additional structural integrity to the composition. The term "dry cellulosic powder" is used herein to describe powders whose internal pores are liquid-free or have a liquid content of less than 50 percent.

DETAILED DESCRIPTION

The examples below illustrate the preparation of liquefiable topical analgesic powders according to the invention.

EXAMPLE 1

A liquefiable powder was prepared by spray evaporative drying. A liquid porogen was prepared from equal parts by weight of menthol and Finsolv TS, an alkyl benzoate oil used in cosmetic preparations. 45 grams of cellulose triacetate was dissolved in 2500 gm of methylene chloride by moderate stirring for 4 hours. To that solution was added 255 gm of the previously prepared porogen diluted with 500 gm of methylene chloride. The resulting homogeneous solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed powder was collected on a fabric filter spanning the bottom of the tower, and the solvent-laden air was passed through carbon beds to collect and recover solvent. The product was transferred to a steel tray and exposed as a 1 cm deep layer in a ventilated hood for 25 minutes to remove residual solvent. Analysis showed 15% cellulose triacetate, 42.5% Finsolv TS, and less than 2 ppm of residual methylene chloride.

EXAMPLE 2

Another analgesic powder was prepared by evaporative spray drying. A liquid porogen was prepared from 15 parts by weight of methyl salicylate and 85 parts by weight of Dow Corning 556 silicone liquid, a cosmetic-grade polyphenylmethylsiloxane. 60 grams of cellulose triacetate was dissolved in 2500 gm of methylene chloride by moderate stirring for 4 hours. To that solution was added 240 gm of the previously prepared porogen diluted with 500 gm of methylene chloride. The resulting homogeneous solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed powder was collected on a fabric filter spanning the bottom of the tower, and the solvent-laden air was passed through carbon beds to collect and recover solvent. The product was transferred to a steel tray and exposed as a 1 cm deep layer in a ventilated hold for 25 minutes to remove residual solvent. Analysis showed 20% cellulose triacetate, 12% methyl salicylate, and 68% silicone liquid, with less than 3 ppm of residual methylene chloride.

EXAMPLE 3

Another analgesic powder was prepared by evaporative spray drying. A liquid porogen was prepared from 15 parts by weight of triethanolamine salicylate and 85 parts by weight of cosmetic grade propylene glycol. 60 grams of cellulose triacetate was dissolved in 3000 gm of methylene chloride by moderate stirring for 4 hours. To that solution was added 240 gm of the previously prepared porogen diluted with 1000 gm of methylene chloride. The resulting homogeneous solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed powder was collected on a fabric filter spanning the bottom of the tower, and the solvent-laden air was passed through carbon beds to collect and recover solvent. The product was transferred to a steel tray and exposed as a 1 cm deep layer in a ventilated hood for 25 minutes to remove residual solvent. Analysis showed 19% cellulose triacetate, 12% triethanolamine salicylate, and 65% propylene glycol, 4% water, and less than 3 ppm of residual methylene chloride.

EXAMPLE 4

40 gr of CTA was dissolved in 520.4 gr of methylene chloride by stirring for one hour. A mixture of 10 gr of phenyltrimethicone (DC 556), 10 gr menthol and 60 gr methyl salicylate were then mixed with 1768.6 gr of methylene chloride. The resulting lacquer was sprayed at 1000 psi from a 0.0135 inch nozzle downwardly into a 100 cm diameter 300 cm high tower through which 110 cfm air was passing from top to bottom through a 4 inch diameter tube. The flow rate was 3.5 gallons of lacquer per hour. The temperature at the top of the tower measured 50.75° C. and the base at 43.15° C., with a relative humidity of 35%.

The resulting product was white and had a smooth feel and a strong menthol odor. The phenyltrimethicone imparts a 'silky, smooth' feel to the resultant powder. The mean particle size was 30.2 mm with 90% of the particles being less than 55.5 mm.

It will be understood that the above description pertains to only several embodiments of the present invention. That is, the description is provided by way of illustration and not by way of limitation. The invention will therefore be further defined according to the following claims.

What is claimed is:

1. An analgesic composition for the delivery of a topical analgesic, the composition comprising a formulation of a frangible, liquid-containing, cellulosic powder formed by spray evaporation and having particles ranging in average diameter from about 1 to about 500 micrometers, the particles further characterized by being microporous with a plurality of interconnecting pores ranging in size from about 1 to about 500 nanometers; and a liquid, analgesic preparation loaded within the pores of the powder particles, such that the liquid containing powder has a liquid content ranging from about 50 percent to about 95 percent by weight, and, upon application and rubbing, the rubbed powder breaks up and the analgesic preparation is readily released.

2. The composition of claim 1 wherein the cellulosic powder is a polymeric powder chosen from the group consisting of cellulose acetates, cellulose butyrates, cellulose nitrates, cellulose propionates, ethyl celluloses, and discrete and molecular mixtures thereof.

3. The composition of claim 1 wherein the analgesic is formulated as a solution by mixing with an emollient.

4. The composition of claim 1 wherein the analgesic preparation comprises a counterirritant.

5. The composition of claim 4 wherein the counterirritant is chosen from the group consisting essentially of salicylates, menthol, camphor, eucalyptol, and mixtures thereof.

6. The composition of claim 1 wherein the analgesic preparation comprises a nonsteroidal, anti-inflammatory (NSAI) agent.

7. The composition of claim 1 wherein the NSAI agent is chosen from the group consisting of aspirin, triethanolamine salicylate, ibuprofen and mixtures thereof.

8. The composition of claim 1 wherein the analgesic preparation comprises a steroidal anti-inflammatory (SAI) agent.

9. The composition of claim 1 wherein the SAI agent is hydrocortisone.

10. The composition of claim 1 wherein the analgesic is formulated as a solution by mixing with an oil.

11. The composition of claim 10 wherein the oil is a mineral oil or silicone oil.

12. The composition of claim 3 wherein the emollient is from the group consisting of isopropyl myristates and palmitates.

13. The composition of claim 12 further including a volatile alcoholic solvent from the group consisting of ethanol and isopropyl alcohol.

14. The composition of claim 3 wherein the emollient is not incorporated within the frangible powder.

* * * * *